(12) United States Patent
Starrett, Jr. et al.

(10) Patent No.: US 8,044,077 B2
(45) Date of Patent: *Oct. 25, 2011

(54) ALPHA-(N-SULFONAMIDO)ACETAMIDE COMPOUNDS INCORPORATING DEUTERIUM AS INHIBITORS OF BETA AMYLOID PEPTIDE PRODUCTION

(75) Inventors: John E. Starrett, Jr., Middletown, CT (US); Kevin W. Gillman, Madison, CT (US); Richard E. Olson, Orange, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/723,936

(22) Filed: Mar. 15, 2010

(65) Prior Publication Data
US 2010/0240719 A1 Sep. 23, 2010

Related U.S. Application Data

(60) Provisional application No. 61/161,629, filed on Mar. 19, 2009.

(51) Int. Cl.
*A61K 31/4245* (2006.01)
*C07D 271/06* (2006.01)
*A61P 25/28* (2006.01)
(52) U.S. Cl. ........................ 514/364; 548/131
(58) Field of Classification Search .................. None
See application file for complete search history.

(56) References Cited

U.S. PATENT DOCUMENTS

| | | | |
|---|---|---|---|
| 5,274,094 A | 12/1993 | Whittaker et al. | |
| 5,516,783 A | 5/1996 | Whittaker et al. | |
| 6,153,612 A | 11/2000 | Ortwine et al. | |
| 6,221,335 B1 * | 4/2001 | Foster | 424/1.81 |
| 6,313,123 B1 | 11/2001 | Levin et al. | |
| 6,603,008 B1 * | 8/2003 | Ando et al. | 546/269.7 |
| 7,300,951 B2 | 11/2007 | Kreft et al. | |
| 7,517,990 B2 * | 4/2009 | Ito et al. | 546/184 |
| 7,687,666 B2 | 3/2010 | Chan et al. | |
| 7,786,122 B2 | 8/2010 | Parker et al. | |
| 7,838,550 B2 | 11/2010 | Chan et al. | |
| 2007/0197695 A1 * | 8/2007 | Potyen et al. | 524/110 |

FOREIGN PATENT DOCUMENTS

| | | |
|---|---|---|
| JP | 11-343279 | 12/1999 |
| WO | WO 98/03166 | 1/1998 |
| WO | WO 00/44716 | 8/2000 |
| WO | WO 00/50391 | 8/2000 |
| WO | WO 03/053912 | 7/2003 |
| WO | WO 2005/042489 | 5/2005 |
| WO | WO 2005/095334 | 10/2005 |
| WO | WO 2006/005486 | 1/2006 |
| WO | WO 2006/034480 | 3/2006 |
| WO | WO 2007/098030 | 8/2007 |
| WO | WO 2008/112249 | 9/2008 |
| WO | WO 2009/005688 | 1/2009 |
| WO | WO 2009/058552 | 5/2009 |
| WO | WO 2009/137657 | 11/2009 |
| WO | WO 2010/107435 | 9/2010 |
| WO | WO 2010/107997 | 9/2010 |
| WO | WO 2010/108067 | 9/2010 |
| WO | WO 2010/120662 | 10/2010 |
| WO | WO 2010/120755 | 10/2010 |

OTHER PUBLICATIONS

Dyck et al. Journal of Neurochemistry, 46(2) (1986) 399-404 ( Abstract Only).*
U.S. Appl. No. 12/840,612, filed Jul. 21, 2010, Parker et al.
Chapman, P.F. et al., "Impaired synaptic plasticity and learning in aged amyloid precursor protein transgenic mice", Nature Neuroscience, vol. 2, No. 3, pp. 271-276 (1999).
Clarke, W.J. et al., "Gender Differences in Oral Drug Exposure in the Rat with the Gamma-Secretase Inhibitor BMS-708163", Drug Metab. Rev., Abstract No. 126, vol. 41, pp. 58-59 (2009).
Dahlgren, K.N. et al., "Oligomeric and Fibrillar Species of Amyloid-β Peptides Differentially Affect Neuronal Viability", The Journal of Biological Chemistry, vol. 277, No. 35, pp. 32046-32053 (2002).
Freebern, W.J. et al., "From Phenotyping to Host Resistance Models: A Comprehensive Immunotoxicologic Investigation of a Gamma Secretase Inhibitor in Rats", International Journal of Toxicology, Abstract No. P12, vol. 29, No. 1, pp. 91-92 (2010).
Gillman, K.W. et al., "Discovery and Evaluation of BMS-708163, a Potent, Selective and Orally Bioavailable γ-Secretase Inhibitor", ACS Medicinal Chemistry Letters, vol. 1, pp. 120-124 (2010).
Golde, T.E., "Alzheimer's disease therapy: Can the amyloid cascade be halted?", The Journal of Clinical Investigation, vol. 111, No. 1, pp. 11-18 (2003).
Götz, J. et al., "Formation of Neurofibrillary Tangles in P301L Tau Transgenic Mice Induced by Aβ 42 Fibrils", Science, vol. 293, pp. 1491-1495 (2001).
Leil, T.A. et al. "Model-Based Trial Simulation for Optimal Collection of CSF Aβ Samples in Clinical Studies: Application for BMS-708163", Clin. Pharmacol. Ther., Abstract No. OII-B-2, vol. 87, Suppl. 1, p. S38 (2010).
Lewis, J. et al., "Enhanced Neurofibrillary Degeneration in Transgenic Mice Expressing Mutant Tau and APP", Science, vol. 293, pp. 1487-1491 (2001).
Loane, D.J. et al., "Amyloid precursor protein secretases as therapeutic targets for traumatic brain injury", Nature Medicine, Advance Online Publication, pp. 1-3 (Mar. 15, 2009).
Maharvi, G.M. et al., "A synthesis of the γ-secretase inhibitor BMS-708163", Tetrahedron Letters, online Oct. 14, 2010.

(Continued)

*Primary Examiner* — Kamal Saeed
(74) *Attorney, Agent, or Firm* — Pamela A. Mingo

(57) ABSTRACT

The present disclosure provides novel deuterated alpha-(N-sulfonamido)acetamide compounds, their pharmaceutical composition, processes thereof and a method for the treatment of Alzheimer's disease, head trauma, traumatic brain injury, and/or dementia pugilistica and/or other conditions associated with β-amyloid peptide.

8 Claims, No Drawings

OTHER PUBLICATIONS

Mayer, S.C. et al., Discovery of Begacestat, a Notch-1-Sparing γ-Secretase Inhibitor for the Treatment of Alzheimer's Disease, Journal of Medicinal Chemistry, vol. 51, No. 23, pp. 7348-7351 (2008).

McLean, C.A. et al., "Soluble Pool of Aβ Amyloid as a Determinant of Severity of Neurodegeneration in Alzheimer's Disease", Annals of Neurology, vol. 46, No. 6, pp. 860-866 (1999).

Seiffert, D. et al., "Presenilin-1 and -2 are Molecular Targets for γ-Secretase Inhibitors", The Journal of Biological Chemistry, vol. 275, No. 44, pp. 34086-34091 (2000).

Selkoe, D.J., "Alzheimer's Disease: Genes, Proteins, and Therapy", Physiological Reviews, vol. 81, No. 2, pp. 741-766 (2001).

Selkoe, D.J., "Cell Biology of the Amyloid β-Protein Precursor and the Mechanism of Alzheimer's Disease", Annu. Rev. Cell Biol., vol. 10, pp. 373-403 (1994).

Siemers, E.R. et al., "Effects of a γ-secretase inhibitor in a randomized study of patients with Alzheimer disease", Neurology, vol. 66, pp. 602-604 (2006).

Thal, D.R. et al., "Two Types of Sporadic Cerebral Amyloid Angiopathy", Journal of Neuropathology and Experimental Neurology, vol. 61, No. 3, pp. 282-293 (2002).

Walsh, D.M. et al., "Naturally secreted oligomers of amyloid β protein potently inhibit hippocampal long-term potentiation in vivo", Nature, vol. 416, pp. 535-539 (2002).

Watkins, T.A. et al., "Distinct Stages of Myelination Regulated by γ-Secretase and Astrocytes in a Rapidly Myelinating CNS Coculture System", Neuron, vol. 60, pp. 555-569 (2008).

Wolfe, M.S., "Secretase Targets for Alzheimer's Disease: Identification and Therapeutic Potential", Journal of Medicinal Chemistry, vol. 44, No. 13, pp. 2039-2060 (2001).

Zhang D. et al., "Disposition of a Gamma-Secretase Inhibitor 14C-Labeled BMS-708163 in Mice, Rats, Rabbits, Dogs, and Humans. Applications of Bile Collection in Differentiating Oxidative Versus Reductive Metabolic Pathways", Drug Metab. Rev., Abstract No. 127, vol. 41, pp. 59-60 (2009).

2008 CSHL Meeting on Neurodegenerative Diseases, Oral Presentation: "BMS-708163, A Potent and Selective Gamma-Secretase Inhibitor, Decreases CSF A-Beta at Safe and Tolerable Doses in Animals and Humans", Dec. 5, 2008.

2009 BMS URG Symposium, Oral Presentation: "The Discovery of BMS-708163: A Potent and Selective Gamma-Secretase Inhibitor for the Treatment of Alzheimer's Disease", May 1, 2009.

237th National American Chemical Society Meeting, Salt Lake City, UT, Oral Presentation: "The Discovery of BMS-708163: A Potent and Selective Gamma-Secretase Inhibitor Which Lowers CSF Beta-Amyloid in Humans", Mar. 22, 2009.

Alzheimer's Association International Conference on Alzheimer's Disease, Chicago, IL, Abstract, Jul. 26, 2008.

Alzheimer's Association International Conference on Alzheimer's Disease, Chicago, IL, Oral Presentation: "BMS-708163, A Potent and Selective Gamma-Secretase Inhibitor, Decreases CSF A-Beta at Safe and Tolerable Doses in Animals and Humans", Jul. 30, 2008.

Alzheimer's Association International Conference on Alzheimer's Disease, Honolulu, HI, Poster: "A Comprehensive Immunotoxicologic Investigation of a Gamma Secretase Inhibitor in Rats", Jul. 10-15, 2010.

Alzheimer's Association International Conference on Alzheimer's Disease, Honolulu, HI, Poster: "A Placebo-Controlled Ascending Multiple-Dose Study to Evaluate the Safety, Pharmacokinetics, and Pharmacodynamics of BMS-708163 in Healthy Young and Elderly Subjects", Jul. 10-15, 2010.

Alzheimer's Association International Conference on Alzheimer's Disease, Honolulu, HI, Poster: "A Study to Evaluate the Effects of Single Oral Doses of BMS-708163 on the Cerebrospinal Fluid A-Beta Level in Healthy Young Men", Jul. 10-15, 2010.

Alzheimer's Association International Conference on Alzheimer's Disease, Honolulu, HI, Poster: "Effect of Concomitant Administration of Multiple Doses of BMS-708163 on Safety and Tolerability and the Pharmacokinetics of Midazolam, Warfarin, Caffeine, Omeprazole, and Dextromethorphan in Healthy Male Subjects by Administration of a Modified Cooperstown Cocktail", Jul. 10-15, 2010.

Alzheimer's Association International Conference on Alzheimer's Disease, Honolulu, HI, Poster: "Gamma-Secretase Inhibitors Have Intrinsically Different Inhibitory Potencies Against A-Beta Production and Notch Signaling", Jul. 10-15, 2010.

Alzheimer's Association International Conference on Alzheimer's Disease, Honolulu, HI, Poster: "Separation of A-Beta Reduction from Notch Toxicity with Gamma-Secretase Inhibitors in Rats", Jul. 10-15, 2010.

Alzheimer's Association International Conference on Alzheimer's Disease, Honolulu, HI, Poster: "The Safety, Tolerability, Pharmacokinetics, and Pharmacodynamics of Single and Multiple Doses of BMS-708163 in Young and Elderly Japanese Subjects", Jul. 10-15, 2010.

Alzheimer's Association International Conference on Alzheimer's Disease, Honolulu, HI, Poster: "The Safety, Tolerability, Pharmacokinetics, and Pharmacodynamics of Single Doses of BMS-708163 in Young and Elderly Subjects", Jul. 10-15, 2010.

American Association of Pharmaceutical Sciences, New Orleans, LA, Oral Presentation: "Simple Allometric Scaling Predicts the Human Dose of BMS-708163, a Gamma Secretase Inhibitor Intended for the Treatment of Alzheimer's Disease", Nov. 14-18, 2010.

AMRI 2010 Integrated Drug Discovery Symposium, Oral Presentation: "Selection and Optimization of a Series of Gamma-Secretase Inhibitors: The Discovery of BMS-708163", Oct. 12-14, 2010.

Bristol-Myers Squibb Symposium, University of California, Irvine, CA, Oral Presentation: "Testing the Amyloid Hypothesis: The Discovery of Brain Penetrant Gamma-Secretase Inhibitors for the Treatment of Alzheimer's Disease", Jun. 2, 2010.

Gordon Research Conference, Newport, RI, Oral Presentation: "Heterocyclic Gamma-Secretase Inhibitors for the Treatment of Alzheimer's Disease", Jun. 30, 2009.

International Society for the Study of Xenobiotics Meeting, Baltimore, MD, Poster: "Gender Differences in Oral Drug Exposure of the Gamma Secretase Inhibitor, BMS-708163, in the Rat", Oct. 18-22, 2009.

Presentation to Department of Chemistry at the University of Arkansas, Fayetteville, AK, Oral Presentation: "Neuroscience Drug Discovery at Bristol-Myers Squibb", Apr. 15, 2010.

U.S. Appl. No. 12/249,180 First Office Action, Apr. 10, 2011.

\* cited by examiner

ALPHA-(N-SULFONAMIDO)ACETAMIDE COMPOUNDS INCORPORATING DEUTERIUM AS INHIBITORS OF BETA AMYLOID PEPTIDE PRODUCTION

CROSS-REFERENCE TO RELATED APPLICATIONS

This application claims the benefit of U.S. Provisional Application Ser. No. 61/161,629 filed Mar. 19, 2009.

FIELD OF THE DISCLOSURE

The present disclosure relates to deuterated (2R)-2-[[(4-chlorophenyl)sulfonyl][[2-fluoro-4-(1,2,4-oxadiazol-3-yl)phenyl]methyl]amino]-5,5,5-trifluoropentanamide compounds having drug and bio-affecting properties, their pharmaceutical compositions, processes thereof and methods of use. The novel compounds possesses a unique inhibition of Aβ peptide production, thereby acting to prevent the accumulation of Aβ peptides and/or amyloid protein deposits in the brain, and are useful in the treatment or delaying the onset of Alzheimer's disease (AD), Down syndrome and mild cognitive impairment as well as in the treatment of head trauma, traumatic brain injury, dementia pugilistica, and/or other conditions associated with β-amyloid peptide.

BACKGROUND

Alzheimer's disease (AD) is a progressive neurodegenerative disease which begins with memory loss and progresses to include severe cognitive impairment, altered behavior, and decreased motor function (Grundman, M. et al., *Arch Neurol.* (2004) 61: 59-66; Walsh, D. M. et al., *Neuron* (2004) 44: 181-193). It is the most common form of dementia and represents the third leading cause of death after cardiovascular disorders and cancer. The cost of AD is enormous and includes the suffering of the patients and families and the lost productivity of patients and caregivers. No treatment that effectively prevents AD or reverses the clinical symptoms and underlying pathophysiology is currently available.

A definitive diagnosis of AD for a demented patient requires a histopathological evaluation of the number and localization of neuritic plaques and neurofibrillary tangles upon autopsy (Consensus recommendations for the postmortem diagnosis of Alzheimer's disease. *Neurobiol Aging* (1997) 18: S1-2). Similar alterations are observed in patients with Trisomy 21 (Down syndrome). Plaques primarily consist of β-amyloid (Aβ) peptides that are formed by a stepwise proteolytic cleavage of the amyloid precursor protein (APP) by β-site APP-cleaving enzyme (BACE), to generate the N-terminus, and γ-secretase, to generate the C-terminus (Selkoe, D. J., *Physiol Rev.* (2001) 81: 741-766). γ-Secretase is a transmembrane protein complex that includes Nicastrin, Aph-1, PEN-2, and either Presenilin-1 (PS-1) or Presenilin-2 (PS-2) (Wolfe, M. S. et al., *Science* (2004) 305: 1119-1123). PS-1 and PS-2 are believed to contain the catalytic sites of γ-secretase.

Aβ40 is the most abundant form of Aβ synthesized (80-90%), while Aβ42 is most closely linked with AD pathogenesis. In particular, mutations in the APP, PS-1, and PS-2 genes that lead to rare, familial forms of AD implicate Aβ42 aggregates as the primary toxic species (Selkoe, D. J., *Physiol Rev.*, (2001) 81: 741-766). Current evidence suggests that oligomeric, protofibrillar and intracellular Aβ42 play a significant role in the disease process (Cleary, J. P. et al., *Nat. Neurosci.* (2005) 8: 79-84). Inhibitors of the enzymes that form Aβ42, such as γ-secretase, represent potential disease-modifying therapeutics for the treatment of AD.

γ-Secretase cleaves multiple type I transmembrane proteins in addition to APP (Pollack, S. J. et al., *Curr Opin Investig Drugs* (2005) 6: 35-47). While the physiological significance of most of these cleavage events is unknown, genetic evidence indicates that γ-secretase cleavage of Notch is required for Notch signaling (Artavanis-Tsakonas, S. et al., *Science* (1999) 284(5415): 770-6; Kadesch, T.; *Exp Cell Res.* (2000) 260(1): 1-8). In rodents dosed with γ-secretase inhibitors, drug-related toxicity has been identified in the gastrointestinal (GI) tract, thymus, and spleen (Searfoss, G. H.; Jordan et al., *J Biol. Chem.* (2003) 278: 46107-46116; Wong, G. T. et al., *J Biol. Chem.* (2004) 279: 12876-12882; Milano, J. et al., *Toxicol Sci.* (2004) 82: 341-358). These toxicities are likely linked to inhibition of Notch signaling (Jensen, J. et al., *Nat. Genet.* (2000) 24: 36-44).

The identification of mechanism-based toxicity raises the question of whether an acceptable therapeutic index can be achieved with γ-secretase inhibitors. Selective inhibition of Aβ formation over Notch processing, pharmacokinetics, drug disposition and/or tissue-specific pharmacodynamics could impact therapeutic margin.

Evidence suggests that a reduction in brain Aβ levels by inhibition of γ-secretase may prevent the onset and progression of AD (Selkoe, D. *Physiol. Rev.* (2001) 81: 741-766; Wolfe, M., *J. Med. Chem.* (2001) 44: 2039-2060). There are emerging data for the role of Aβ in other diseases, including mild cognitive impairment (MCI), Down syndrome, cerebral amyloid angiopathy (CAA), dementia with Lewy bodies (DLB), amyotrophic lateral sclerosis (ALS-D), inclusion body myositis (IBM), and age-related macular degeneration. Advantageously, compounds that inhibit γ-secretase and reduce production of Aβ could be used to treat these or other Aβ-dependent diseases.

Excess production and/or reduced clearance of Aβ causes CAA (Thal, D. et al., *J. Neuropath. Exp. Neuro.* (2002) 61: 282-293). In these patients, vascular amyloid deposits cause degeneration of vessel walls and aneurysms that may be responsible for 10-15% of hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients. Compounds that specifically target γ-secretase could reduce or prevent CAA.

DLB manifests with visual hallucinations, delusions, and parkinsonism. Interestingly, familial AD mutations that cause Aβ deposits can also cause Lewy bodies and DLB symptoms (Yokota, O. et al., *Acta Neuropathol (Berl)* (2002) 104: 637-648). Further, sporadic DLB patients have Aβ deposits similar to those in AD (Deramecourt, V. et al., *J Neuropathol Exp Neurol* (2006) 65: 278-288). Based on this data, Aβ likely drives Lewy body pathology in DLB and, therefore, γ-secretase inhibitors could reduce or prevent DLB.

Approximately 25% of ALS patients have significant dementia or aphasia (Hamilton, R. L. et al., *Acta Neuropathol (Berl)* (2004) 107: 515-522). The majority (~60%) of these patients, designated ALS-D, contain ubiquitin-positive inclusions comprised primarily of the TDP-43 protein (Neumann, M. et al., *Science* (2006) 314: 130-133). About 30% of the ALS-D patients have amyloid plaques consistent with Aβ causing their dementia (Hamilton, R. L. et al., *Acta Neuropathol (Berl)* (2004) 107: 515-522). These patients should be identifiable with amyloid imaging agents and potentially treatable with γ-secretase inhibitors.

IBM is a rare, age-related degenerative disease of skeletal muscle. The appearance of Aβ deposits in IBM muscle and the recapitulation of several aspects of the disease by directing APP overexpression to muscle in transgenic mice support the role of Aβ in IBM (reviewed in Murphy, M. P. et al., *Neurology* (2006) 66: S65-68). Compounds that specifically target γ-secretase could reduce or prevent IBM.

In age-related macular degeneration, Aβ was identified as one of several components of drusen, extracellular deposits beneath the retinal pigment epithelium (RPE) (Anderson, D. H. et al., *Exp Eye Res* (2004) 78: 243-256). A recent study has shown potential links between. Aβ and macular degeneration in mice (Yoshida, T. et al., *J Clin Invest* (2005) 115: 2793-2800). Increases in Aβ deposition and supranuclear cataracts have been found in AD patients (Goldstein, L. E. et al., *Lancet* (2003) 361: 1258-1265). Compounds that specifically target γ-secretase could reduce or prevent age-related macular degeneration.

Based on the role of Notch signaling in tumorigenesis, compounds which inhibit γ-secretase may also be useful as therapeutic agents for the treatment of cancer (Shih, I.-M., et al., *Cancer Research* (2007) 67: 1879-1882).

Compounds which inhibit gamma secretase may also be useful in treating conditions associated with loss of myelination, for example multiple sclerosis (Watkins, T. A., et al., Neuron (2008) 60: 555-569).

A recent study by Georgetown University Medical Center researchers suggests that gamma-secretase inhibitors may prevent long-term damage from traumatic brain injury (Loane, D. J., et al., *Nature Medicine* (2009): 1-3).

Smith, et al. in International Application WO 00/50391, published Aug. 31, 2000, disclose a series of sulfonamide compounds that can act to modulate production of amyloid β protein as a means of treating a variety of diseases, especially Alzheimer's disease and other diseases relating to the deposition of amyloid.

Japanese Patent No. 11343279, published Dec. 14, 1999 discloses a series of sulfonamide derivatives which are TNF-alpha inhibitors useful for treating autoimmune diseases.

Parker, et al. in International Application WO 03/053912, published Jul. 3, 2003, disclose a series of α-(N-sulphonamido)acetamide derivatives as β-amyloid inhibitors which are useful for the treatment of Alzheimer's disease and other conditions associated with β-amyloid peptide.

The present disclosure provides a compound useful for the treatment of Alzheimer's disease and other conditions associated with β-amyloid peptide.

DESCRIPTION OF THE DISCLOSURE

The present disclosure relates to deuterated (2R)-2-[[(4-chlorophenyl)sulfonyl][[2-fluoro-4-(1,2,4-oxadiazol-3-yl)phenyl]methyl]amino]-5,5,5-trifluoropentanamide compounds having the Formula I, their pharmaceutical formulations, and their use in inhibiting Aβ production in patients suffering from or susceptible to Alzheimer's disease (AD) or other disorders associated with β-amyloid peptide, where compounds of Formula I contain one or more deuterium atoms.

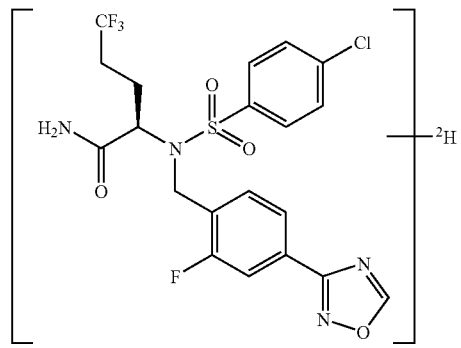

In one aspect of the present disclosure, the deuterium is attached to the oxadiazole ring, as shown in Formula I-A.

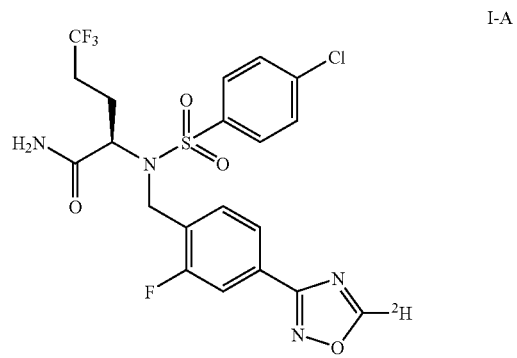

In another embodiment, the present disclosure provides a pharmaceutical composition comprising a therapeutically effective amount of a deuterated (2R)-2-[[(4-chlorophenyl) sulfonyl][[2-fluoro-4-(1,2,4-oxadiazol-3-yl)phenyl]methyl] amino]-5,5,5-trifluoropentanamide compound in association with a pharmaceutically acceptable adjuvant, carrier or diluent.

In yet another embodiment, the present disclosure provides a method for the treatment, alleviation or delaying the onset of disorders associated with β-amyloid peptide, especially Alzheimer's disease, cerebral amyloid angiopathy, mild cognitive impairment, and Down syndrome which comprises administering together with a conventional adjuvant, carrier or diluent a therapeutically effective amount of a deuterated (2R)-2-[[(4-chlorophenyl)sulfonyl][[2-fluoro-4-(1,2,4-oxadiazol-3-yl)phenyl]methyl]amino]-5,5,5-trifluoropentanamide compound or solvate or hydrate thereof.

In another aspect, the present disclosure provides a process for the preparation of (2R)-2-[[(4-chlorophenyl)sulfonyl][[2-fluoro-4-(1,2,4-oxadiazol-5-deutero-3-yl)phenyl]methyl] amino]-5,5,5-trifluoropentanamide comprising the step of reacting (R)-2-(4-chlorophenylsulfonamido)-5,5,5-trifluoropentanamide with 3-(4-(bromomethyl)-3-fluorophenyl)-5-deutero-1,2,4-oxadiazole in an inert organic solvent in the presence of a base and preferably an inorganic base such as cesium carbonate.

In still another aspect, the present disclosure provides a process for the preparation of (2R)-2-[[(4-chlorophenyl)sulfonyl][[2-fluoro-4-(1,2,4-oxadiazol-5-deutero-3-yl)phenyl] methyl]amino]-5,5,5-trifluoropentanamide comprising the steps of:

(a) reacting (R)-2-(4-chloro-N-(4-cyano-2-fluorobenzyl)phenylsulfonamido)-5,5,5-trifluoropentanamide with hydroxylamine, and (b) treating the resulting (R)-2-(4-chloro-N-(2-fluoro-4-(N-hydroxycarbamimidoyl)benzyl)phenylsulfonamido)-5,5,5-trifluoropentanamide with triethyl orthoformate-D in an inert organic solvent in the presence of an acid catalyst.

As the compound of the present disclosure possesses an asymmetric carbon atom, the present disclosure includes the racemate as well as the individual enantiometric forms of the compound of Formula I and chiral and racemic intermediates as described herein. The use of a single designation such as (R) or (S) is intended to include mostly one stereoisomer. Mixtures of isomers can be separated into individual isomers according to known methods, e.g. fractional crystallization, adsorption chromatography or other suitable separation processes. Resulting racemates can be separated into antipodes in the usual manner after introduction of suitable salt-forming groupings, e.g. by fanning a mixture of diastereosiomeric salts with optically active salt-forming agents, separating the mixture into diastereomeric salts and converting the separated salts into the free compounds. The enantiomeric forms may also be separated by fractionation through chiral high pressure liquid chromatography columns. It is understood that deuterium incorporation in Formulas or schemes may be indicated by use of the symbols "D", "d" or "²H".

In the method of the present disclosure, the term "therapeutically effective amount" means the total amount of each active component of the method that is sufficient to show a meaningful patient benefit, i.e., healing of conditions associated with β-amyloid peptide. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, delaying, suppressing or ameliorating diseases associated with β-amyloid peptide.

In still yet another embodiment of the disclosure, the compound of Formula I may be used in combination with other drugs that are used in the treatment/prevention/suppression or amelioration of the diseases or conditions for which the compound of Formula I is useful. Such other drugs may be administered by a route and in an amount commonly used therefor, contemporaneously or sequentially with the compound of the present disclosure. When the compound of Formula I is used contemporaneously with one or more other drugs, a pharmaceutical composition containing such drugs in addition to the compound of Formula I is preferred. Accordingly, the pharmaceutical compositions of the present disclosure include those that also contain one or more other active ingredients, in addition to the compound of Formula I. Examples of other active ingredients that may be combined with, for example, (2R)-2-[[(4-chlorophenyl)sulfonyl][[2-fluoro-4-(1,2,4-oxadiazol-5-deutero-3-yl)phenyl]methyl]amino]-5,5,5-trifluoropentanamide, either administered separately or in the same pharmaceutical compositions, to treat Alzheimer's disease include, but are not limited to: the class of drugs which are cholinesterase inhibitors, for example donepezil (Aricept®), rivastigmine (Exelon®, galantamine (Reminyl®, now Razadyne®; other drugs which are NMDA antagonists such as memantine Namenda®) and PDE4 inhibitors such as cilomilast (Ariflo®); the class of NSAIDs, such as R-flurbiprofen (Flurizan®); the cholesterol-lowering statin drugs such as pravastatin, simvastatin, and atorvastatin; anti-amyloid and anti-Aβ immune therapy; compounds which inhibit the aggregation of Aβ, such as scylloinositol and clioquinol; other compounds which inhibit or modify Aβ production or processing such as γ-secretase inhibitors, J-secretase inhibitors, γ-secretase modulators, Aβ modulators, and GSK-3 inhibitors; compounds which regulate Aβ turnover such as PAI-1 inhibitors; compounds which regulate tau phosphorylation such as GSK-3 and CDK-5 inhibitors; PPARγ agonists such as rosiglitazone; compounds which regulate tau or phosphor-tau turnover, or oligomerization such as HSP90 inhibitors, HDAC inhibitors and anti-tau immune therapy; and compounds which stabilize or bind to microtubules, such as taxane derivatives and epothilone derivatives; and compounds which regulate mitochondria function such as Dimebon.

In the treatment of cancer, the compound of the present disclosure may be used with known anti-cancer agents or treatments. Such agents and treatments include cytotoxic/cytostatic agents, androgen receptor modulators, estrogen receptor modulators, retinoid receptor modulators, prenylprotein transferase inhibitors, angiogenesis inhibitors, agents that interfere with cell-cycle checkpoints, and radiation therapy. In addition, the compounds of the present disclosure may be useful in the treatment of immunological disorders such as Lupus.

The above therapeutic agents, when employed in combination with the compound of the present disclosure, may be used, for example, in those amounts indicated in the Physician's Desk Reference (PDR), where applicable or as otherwise determined by one of ordinary skill in the art.

However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms.

General Reaction Schemes

The compound of the present disclosure can be prepared in a number of different ways well-known to one skilled in the art of organic synthesis. The compounds of Formula I can be prepared by the methods described below in Reaction Schemes 1-5. Reasonable variations of the described procedures, together with synthetic methods which would be evident to one skilled in the art, are intended to be within the scope of the present disclosure.

Reaction Scheme 1

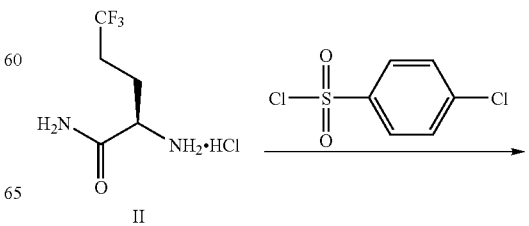

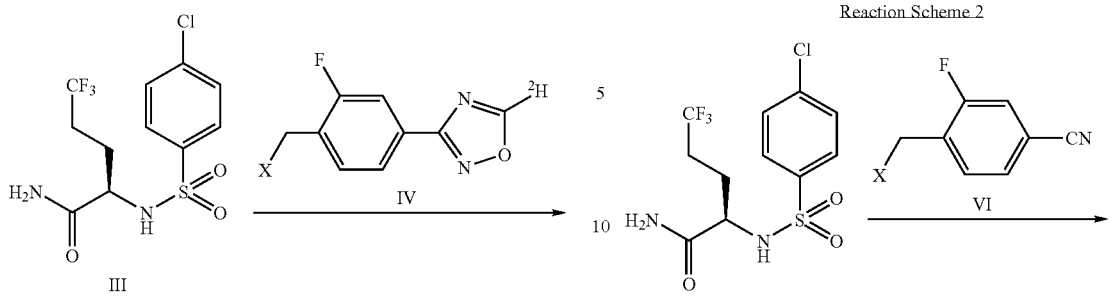

In one method of preparation illustrated in Reaction Scheme 1, the starting (α-amino)acetamide of Formula II which is used in substantially enantiomerically pure form may be prepared by well-known literature procedures such as using the asymmetric Strecker synthesis method described in Reaction Scheme 3 for the conversion of trifluorobutyraldehyde to the (α-amino)acetamide of Formula II, or alternatively from (R)-5,5,5-trifluoronorvaline (see; I. Ojima, *J. Org. Chem.* (1989) 54: 4511-4522) and the method described in Reaction Scheme 4 followed by the general procedures for amide preparation: R. C. Larock "Comprehensive Organic Transformations", VCH Publishers, New York, 1989, pp. 972-976. The (α-amino)acetamide of Formula II is treated with a suitable base and sulfonylated with p-chlorosulphonyl chloride in a suitable aprotic solvent such as $CH_2Cl_2$ at about room temperature to afford the (a-sulfonamido)acetamide of Formula III. Suitable bases include triethylamine, diisopropylamine, pyridine and the like.

The conversion of the compound of Formula III to the sulfonamide of Formula I-A is carried out in the presence of a base by reacting the (α-sulfonamido)acetamide of Formula III with a deuterated oxadiazole fluorobenzyl alkylating agent of Formula IV in a suitable aprotic solvent with or without heating. The fluorobenzyl deuterated oxadiazole of Formula IV may readily be prepared by methods well-known in the art wherein X is a leaving group and by the method described in Reaction Scheme 6. Suitable bases for this alkylation include inorganic bases such as potassium carbonate and cesium carbonate. Preferred solvents include DMF and acetonitrile. The temperature range for the reaction is typically 20° C. to 100° C.

In another method of preparation illustrated in Reaction Scheme 2, the 1,2,4-oxadiazole compound of Formula I-A is prepared by alkylating the compound of Formula III with 2-cyano-4-fluorobenzyl derivative of Formula VI wherein X is a leaving group in the presence of a base in a suitable solvent to produce the nitrile of Formula VII. The desired compound of Formula I-A is then prepared from the nitrile compound of Formula VII using methods well-known to those skilled in the art (ref: Joule, J. A, et al., *Heterocyclic Chemistry*, 3rd ed., Chapman & Hall, London (1995) 452-456 and references cited therein). For example, reaction of the nitrile of Formula VII with hydroxylamine in an alcohol solvent such as methanol or ethanol at temperatures up to reflux provides an intermediate amide oxime that is subsequently treated with a deutero-orthoformate (such as triethyl or trimethyl orthoformate-D) in the presence of an acid source such as trifluoroacetic acid or boron trifluoride etherate in an inert organic solvent such as $CH_2Cl_2$, acetonitrile, tetrahydrofuran and the like to provide the 1,2,4-oxadiazole of Formula I-A.

Reaction Scheme 3

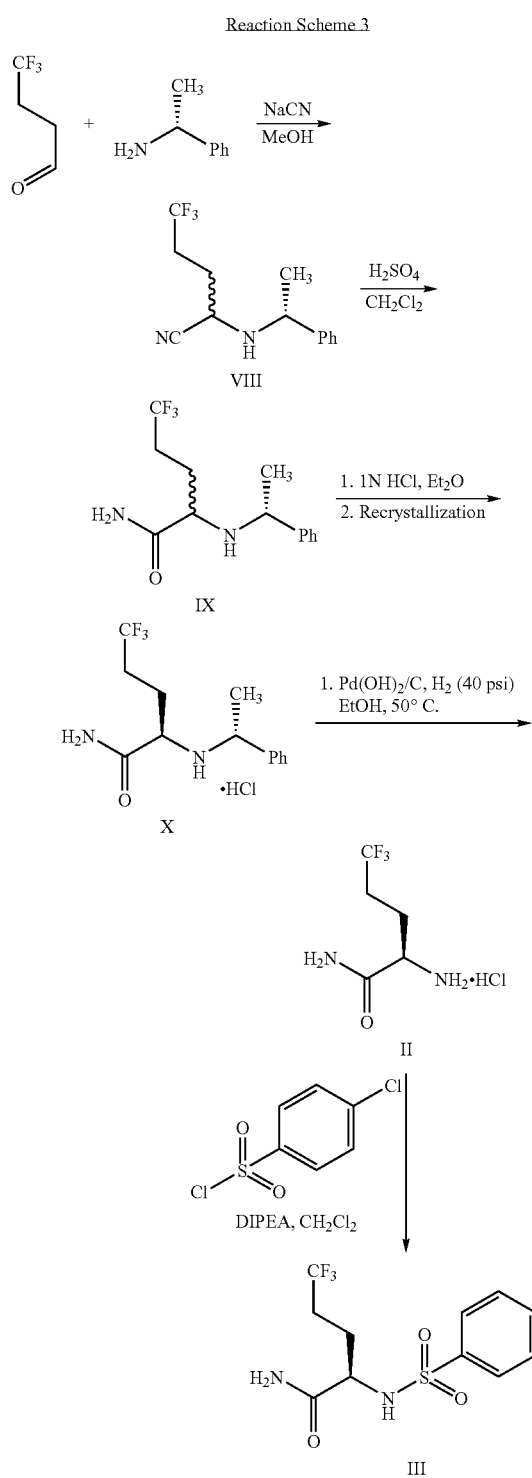

Reaction Scheme 3 describes the preparation of (α-amino)acetamide of Formula II starting with commercially available trifluorobutyraldehyde and (R)-α-methyl benzyl amine under Strecker conditions with acetic acid and cyanide source such as sodium cyanide, potassium cyanide, or trimethylsilylcyanide in a suitable solvent such as methanol to afford the aminonitrile of Formula VIII as a mixture of diastereomers. The starting trifluorobutyraldehyde may also be prepared by oxidation of trifluorobutanol. Hydrolysis of the nitrile of Formula VIII to the corresponding amide of Formula IX is carried out with sulfuric acid and neutralization of the reaction, followed by acidification and recrystallization from a suitable solvent such as methanol, isopropanol, ethyl acetate, methyl tert-butyl ether, or mixtures thereof, to afford the amide of Formula X in >99% diastereomeric excess. The benzyl group may then be removed by hydrogenation in the presence of a suitable catalyst such as palladium hydroxide or palladium on carbon to give the amino amide of Formula II which may be sulfonylated with p-chlorosulphonyl chloride to afford the sulfonamide of Formula III.

Reaction Scheme 4

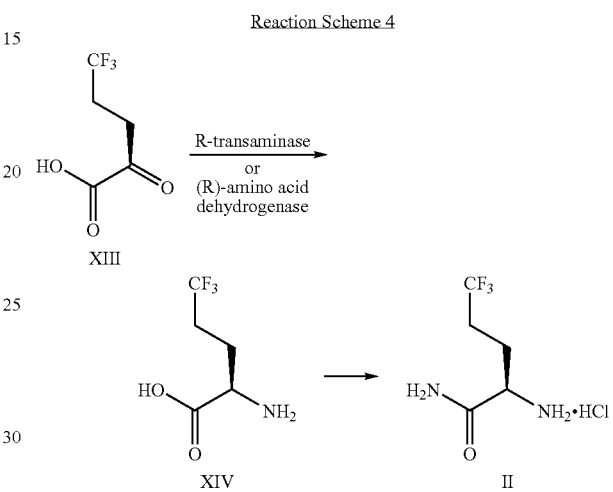

In another method of preparation, the (α-amino)acetamide of Formula II can be stereoselectivity produced using an enzymatic process starting with 5,5,5-trifluoro-2-oxopentanoic acid as illustrated in Reaction Scheme 4. The (R)-5,5,5-trifluoronorvaline of Formula XIV may be prepared in substantially enantiomerically pure form from the compound of Formula XIII using commercially available (R)-aminotransferase enzyme by methods well known to those skilled in the art. In an alternate method, the enzymatic process may be carried out using the commercially available (R)-amino acid dehydrogenase enzyme. The enzymatic processes are carried out using the methods described below and methods well-known to those skilled in the art. The conversion of the (R)-5,5,5-trifluoronorvaline of Formula XIV to the compound of Formula II may be carried out using general procedures for amide preparation well-known in the art.

Reaction Scheme 5

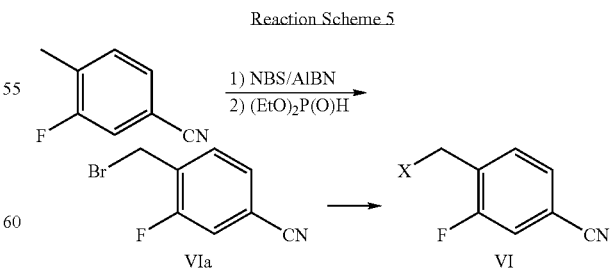

Benzyl bromide of Formula VIa may be prepared by bromination of commercially available 2-fluoro-4-cyanotoluene with N-bromosuccinimide in a suitable solvent such as dichloromethane, dichloroethane or carbon tetrachloride, using an initiator such as AIBN as illustrated in Reaction Scheme 5. The bromination proceeds in high yield and, if desired, the compound of Formula VIa may readily be converted to the compound of Formula VI wherein X is a leaving group by methods well-known to those skilled in the art.

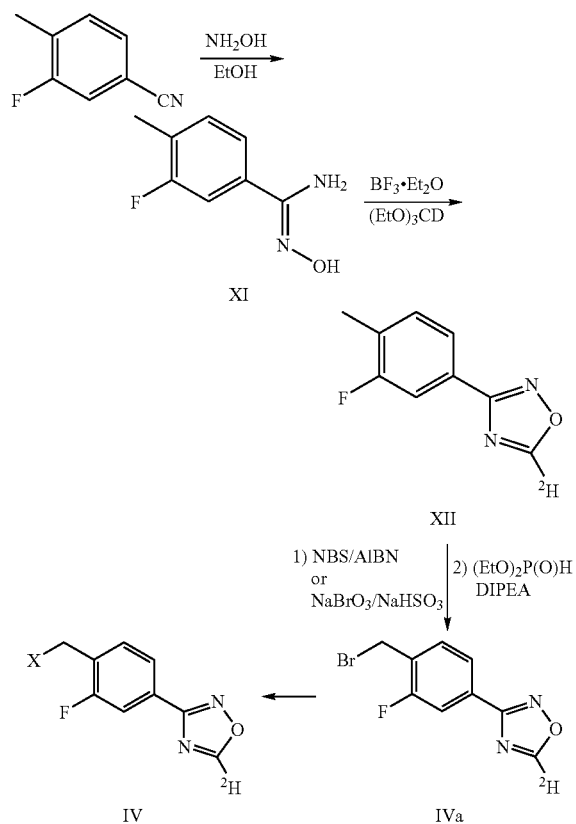

As an alternative to the use of the compound of Formula VI in the linear sequence to the sulfonamide oxadiazole of Formula I-A described above in Reaction Scheme 2, the preparation of the compound of Formula IV for use in the convergent route depicted in Reaction Scheme 1 is shown in Reaction Scheme 6. Treatment of commercially available 2-fluoro-4-cyanotoluene with hydroxylamine at room temperature in an alcohol solvent affords crude amide oxime of Formula XI, which may be directly employed in the subsequent reaction. Cyclization of the amide oxime of Formula XI by treatment with boron trifluoride etherate and triethyl orthoformate-D affords the oxadiazole of Formula XII in over 90% yield in two steps. As an alternative to the use of boron trifluoride, the cyclization can also be cleanly accomplished by employing trifluoroacetic acid as the acid source. Bromination with N-bromosuccinimide in a suitable solvent such as dichloromethane, dichloroethane, or carbon tetrachloride using an initiator such as AIBN affords the mono-bromo deuterated oxadiazole compound of Formula IVa. If it is desired to avoid possible mixtures of mono- and di-bromides, the toluoyl function of compound of Formula XI may deliberately be overbrominated with N-bromosuccinimide and AIBN to afford the corresponding dibromide which may then be reduced with diethyl phosphite to afford the mono-bromide of Formula VIa in over 90% yield. The dibromination and reduction may be accomplished in one pot without isolation of the dibromide in an overall yield of over 90%. Alternatively, the compound of Formula IVa may also be prepared from the compound of Formula XII with excess sodium bromate and sodium bisulfite in a suitable two-phase solvent system such as ethyl acetate/water, dichloromethane/water, butyl acetate/water, trifluorotoluene/water and the like to provide a mixture of mono- and di-bromide intermediates which is reduced in situ with diethyl phosphate/diisopropylamine to afford the mono-bromide of Formula IVa. If desired, the compound of Formula IVa may readily be converted to the compound of Formula IV wherein X is a leaving group by methods well-known to those skilled in the art.

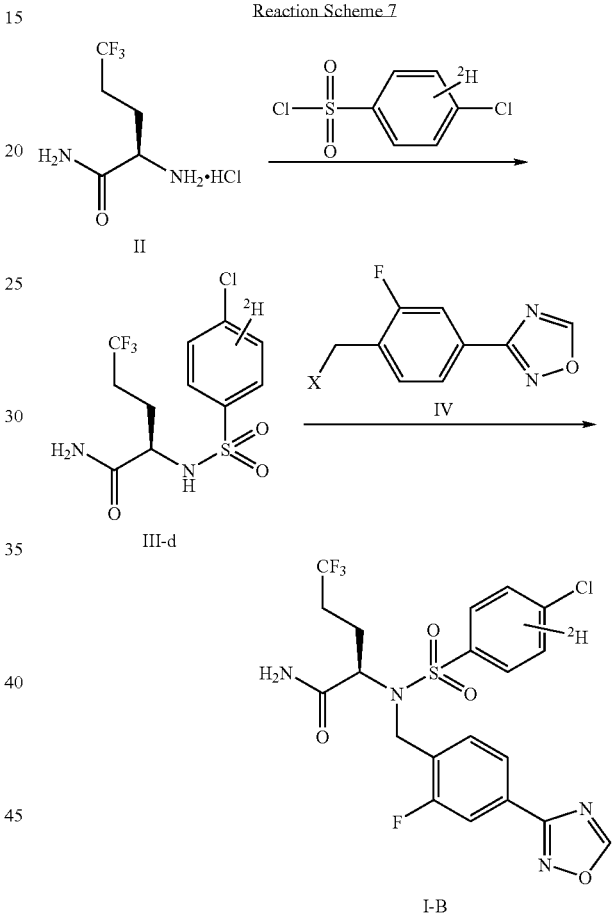

As is apparent to one skilled in the art, deuterium atoms may be incorporated in various starting materials used in the preparation of compounds of Formula I. For example, the use of a sulfonyl chloride incorporating one or more deuterium atoms in the sulfonylation of amino amide II will provide a deuterated sulfonamide III-d, which may be used in the preparation of compounds of Formula I-B as illustrated in Scheme 7. Such methods may be used to incorporate one or more deuterium atoms in desired positions in compounds of Formula I. DE10162121A1 provides a synthesis of 2,3,5,6-tetradeutero-4-chlorobenzenesulfonyl chloride, useful in the preparation of Compounds of Formula I containing deuterium on the sulfonamide phenyl ring.

In another embodiment, this disclosure includes pharmaceutical compositions comprising the compound of Formula I in combination with a pharmaceutical adjuvant, carrier or diluent.

In still another embodiment, this disclosure relates to a method of treatment of disorders responsive to the inhibition of β-amyloid peptide in a mammal in need thereof, which comprises administering to said mammal a therapeutically effective amount of the compound of Formula I or a solvate or hydrate thereof.

In yet another embodiment, this disclosure relates to a method for treating, alleviating or delaying the onset of Alzheimer's disease, cerebral amyloid angiopathy, systemic amyloidosis, hereditary cerebral hemorrhage with amyloidosis of the Dutch type, multi-infarct dementia, mild cognitive impairment and Down syndrome in a patient in need thereof, which comprises administering to said patient a therapeutically effective amount of the compound of Formula I or solvate or hydrate thereof.

In yet another embodiment, this invention relates to a method for the treatment of head trauma, traumatic brain injury, and/or dementia pugilistica, which comprises administering to a mammal in need thereof a therapeutically effective amount of the compound of Formula I or a solvate or hydrate thereof.

In yet another embodiment, this invention relates to a method for the treatment of head trauma which comprises administering to a mammal in need thereof a therapeutically effective amount of the compound of Formula I or a solvate or hydrate thereof.

In yet another embodiment, this invention relates to a method for the treatment of traumatic brain injury which comprises administering to a mammal in need thereof a therapeutically effective amount of the compound of Formula I or a solvate or hydrate thereof.

In yet another embodiment, this invention relates to a method for the treatment of dementia pugilistica which comprises administering to a mammal in need thereof a therapeutically effective amount of the compound of Formula I or a solvate or hydrate thereof.

For therapeutic use, the pharmacologically active compound of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous), transdermal, sublingual, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. Oral preparations include push-fit capsules made of gelatin, as well as soft, scaled capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. For topical or nasal administration, penetrants or permeation agents that are appropriate to the particular barrier to be permeated are used in the formulation. Such penetrants are generally known in the art. The pharmaceutical compositions are prepared by conventional techniques appropriate to the desired preparation containing appropriate amounts of the active ingredient, that is, the compound of Formula I according to the disclosure. See, for example, *Remington's Pharmaceutical Sciences*, Mack Publishing Company, Easton, Pa., 17th edition, 1985.

The dosage of the compound of Formula I to achieve a therapeutic effect will depend not only on such factors as the age, weight and sex of the patient and mode of administration, but also on the degree of Aβ inhibition desired and the potency of the compound of Formula I for the particular disorder or disease concerned. It is also contemplated that the treatment and dosage of the compound of Formula I may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this disclosure to produce the desired therapeutic effect.

A suitable dose of the compound of Formula I or pharmaceutical composition thereof for a mammal, including man, suffering from, or likely to suffer from any condition related to Aβ peptide production as described herein, generally the daily dose will be from about 0.01 mg/kg to about 10 mg/kg and preferably, about 0.1 to 2 mg/kg when administered parenterally. For oral administration, the dose may be in the range from about 0.01 to about 20 mg/kg and preferably from 0.1 to 10 mg/kg body weight. The active ingredient will preferably be administered in equal doses from one to four times a day. However, usually a small dosage is administered, and the dosage is gradually increased until the optimal dosage for the host under treatment is determined. In accordance with good clinical practice, it is preferred to administer the instant compound at a concentration level that will produce an effective anti-amyloid effect without causing any harmful or untoward side effects. However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

Biological Data

In Vitro Pharmacology
Inhibition of Aβ Formation in Cultured Cells

Compounds were assayed for Aβ42 inhibition in cells using H4 APP751 SWE clone 8.20, developed at Bristol-Myers Squibb, an H4 neuroglioma cell line stably expressing the Swedish mutant of APP751. Cells were maintained in log phase through twice weekly passage at a 1:20 dilution. For IC$_{50}$ determinations, 30 μL cells (1.5×10$^4$ cells/well) in DMEM media containing 0.0125% BSA (Sigma A8412) were plated directly into 384-well compound plates (Costar 3709) containing 0.1 μL serially diluted compound in DMSO. Following incubation for 19 hours in 5% CO$_2$ at 37° C., plates were briefly centrifuged (1000 rpm, 5 min). Antibody cocktails were freshly prepared by dilution into 40 mM Tris-HCl (pH 7.4) with 0.2% BSA and added to assay plates. For Aβ42 measurements, antibodies specific for the Aβ42 neoepitope (565, developed at Bristol-Myers Squibb; conjugated to the Wallac reagent (Perkin Elmer)) and the N-terminal sequence of Aβ peptide (26D6, developed at SIBIA/Bristol-Myers Squibb; conjugated to APC (Perkin Elmer)) were mixed and 20 μL of the mixture was added to each well of the incubated cell plate yielding a final concentration of 0.8 ng/well 565 and 75 ng/well 26D6. Assay plates containing antibodies were sealed with aluminum foil and incubated overnight at 4° C. Signal was determined using a Viewlux counter (Perkin Elmer) and IC$_{50}$ values determined using curve fitting in CurveMaster (Excel Fit based).

(2R)-2-[[(4-Chlorophenyl)sulfonyl][[2-fluoro-4-(1,2,4-oxadiazol-5-deutero-3-yl)phenyl]methyl]amino]-5,5,5-trifluoropentanamide potently inhibited the formation of Aβ42 in H4-8Sw cells. Analysis yielded IC$_{50}$=0.12±0.01 nM (mean±SD, n=2) for Aβ42 inhibition.

The above results confirm that (2R)-2-[[(4-chlorophenyl)sulfonyl][[2-fluoro-4-(1,2,4-oxadiazol-5-deutero-3-yl)phenyl]methyl]amino]-5,5,5-trifluoropentanamide is a potent γ-secretase inhibitor. These results support the use of (2R)-2-[[(4-chlorophenyl)sulfonyl][[2-fluoro-4-(1,2,4-oxadiazol-5-deutero-3-yl)phenyl]methyl]amino]-5,5,5-trifluoropentanamide as a therapeutic treatment for Alzheimer's disease, head trauma, traumatic brain injury, dementia pugilistica, and/or other disorders associated with β-amyloid peptide.

The following examples are given by way of illustration and are not to be construed as limiting the disclosure in any way inasmuch as variations of the disclosure are possible within the spirit of the disclosure.

The compounds of the present application can be prepared in a number of ways well known to one skilled in the art of organic synthesis. The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The compounds may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

DESCRIPTION OF THE SPECIFIC EMBODIMENTS

In the following examples, all temperatures are given in degrees Centigrade. Melting points were recorded on a Thomas Scientific Unimelt capillary melting point apparatus and are uncorrected. Proton magnetic resonance ($^1$H NMR) spectra were recorded on a Broker Avance 300, a Bruker Avance 400, or a Broker Avance 500 spectrometer. All spectra were determined in the solvents indicated and chemical shifts are reported in δ units downfield from the internal standard tetramethylsilane (TMS) and interproton coupling constants are reported in Hertz (Hz). Multiplicity patterns are designated as follows: s, singlet; d, doublet; t, triplet; q, quartet; m, multiplet; br, broad peak; dd, doublet of doublet; br d, broad doublet; dt, doublet of triplet; br s, broad singlet; dq, doublet of quartet. Infrared (IR) spectra using potassium bromide (KBr) or sodium chloride film were determined on a Jasco FT/IR-410 or a Perkin Elmer 2000 FT-IR spectrometer from 4000 cm$^{-1}$ to 400 cm$^{-1}$, calibrated to 1601 cm$^{-1}$ absorption of a polystyrene film and reported in reciprocal centimeters (cm$^{-1}$). Optical rotations [α]$_D$ were determined on a Rudolph Scientific Autopol IV polarimeter in the solvents indicated; concentrations are given in mg/mL. Low resolution mass spectra (MS) and the apparent molecular (MH$^+$) or (M–H)$^+$ was determined on a Finnegan SSQ7000. High resolution mass spectra were determined on a Finnegan MAT900. Liquid chromatography (LC)/mass spectra were run on a Shimadzu LC coupled to a Water Micromass ZQ.

The following abbreviations are used: DMF (dimethylformamide); THF (tetrahydrofuran); DMSO (dimethylsulfoxide), Leu (leucine); TFA (trifluoroacetic acid); MTBE (methyltertbutylether); DAST [(diethylamino)sulfur trifluoride], HPLC (high pressure liquid chromatography); rt (room temperature); aq. (aqueous); AP (area percent).

Preparation A (R)-2-Amino-5,5,5-trifluoropentanamide hydrochloride

Step A. 4,4,4-Trifluorobutanol

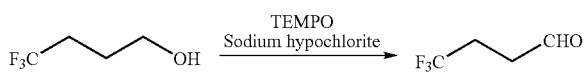

Dichloromethane (4.2 L) was charged into a 20 L four necked round bottom flask, equipped with mechanical stirring and cooling bath. The stirring was started and the reaction mixture cooled to 0 to –2° C. 4,4,4-Trifluorobutanol (750.0 g) was charged and the reaction mixture was cooled further to –5 to –8° C. TEMPO; (2,2,6,6-tetramethyl-1-piperidinyloxy, free radical) (9.15 g) was added while keeping the temperature between –5 to –8° C. An aqueous solution of potassium bromide (60 g in 1.17 L of water) was added to the above solution and the temperature was maintained at –5 to –8° C. An aqueous solution of NaOCl (8.8 L, 6-7% by wt., buffered to pH=8.5 using sodium bicarbonate) was added to the reaction mixture (caution: exothermic) while keeping the temperature of the reaction mixture at –5° C. Similarly, sodium periodate (NaIO$_4$) can substitute for NaOCl as the oxidizing agent. After complete addition, the dichloromethane layer was separated and the aqueous layer was washed with dichloromethane (1×750 mL). The dichloromethane layers were combined and dried using anhydrous sodium sulfate. The drying agent was filtered, and concentration of the solution of 4,4,4-trifluorobutanol was determined by NMR. The solution containing the title compound was used directly in the next step without additional processing.

$^1$H NMR (CDCl$_3$) (400 MHz) δ 2.30-2.50 (m, 2H, CH$_2$—CF$_3$), 2.70-2.80 (m, 2H, CH$_2$—CHO), 9.8 (s, 1H, CHO).

Step B. 5,5,5-Trifluoro-2-(1-phenylethylamino)pentanenitrile (mixture of diastereomers)

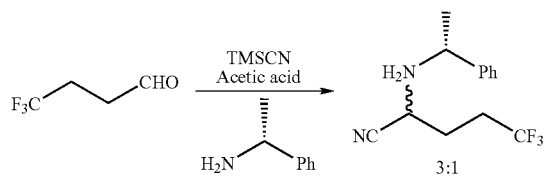

R-α-Methyl benzyl amine (528.5 g) was charged into a suitable vessel equipped with mechanical stirring, cooling bath and maintained under a blanket of nitrogen. 4,4,4-Trifluorobutyraldehyde solution (from Step A, 550 g) was charged, followed by methanol (3.3 L). The reaction mixture was then cooled to about 0 to −3° C. Acetic acid (glacial, 260 mL) was added drop-wise, maintaining the temperature around 0° C. followed by trimethylsilyl cyanide (581 mL) over a period of 15 minutes. Similarly, sodium cyanide (NaCN) or potassium cyanide could be used as the cyanide source. The reaction mixture was warmed to 25 to 27° C. and stirred overnight. Completion of the reaction was determined by TLC. Chilled Water (10.0 L) was charged into the reaction mixture and the reaction mixture was extracted with dichloromethane (1×10.0 L). The dichloromethane layer was washed with water (2×10.0 L) followed by brine (1×5.0 L). The dichloromethane layer was dried over anhydrous sodium sulfate and concentrated under reduced pressure to yield the title aminonitrile (mixture of diastereomers) as a viscous liquid, average yield 90%. $^1$H NMR (CDCl$_3$) (400 MHz) δ 1.42 (d&m, 5H), 2.15 & 2.35 (two in, 1H each), 3.10-3.20 (m, 1H), 4.10-4.15 (m, 1H), 7.10-7.35 (m, 6H).

Step C.
5,5,5-Trifluoro-2-(1-phenylethylamino)pentanamide (mixture of diastereomers)

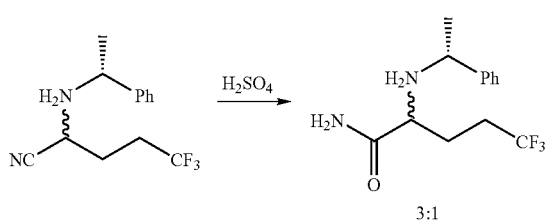

5,5,5-Trifluoro-2-(1-phenylethylamino)pentanenitrile (crude mixture of diastereomers from Step B, 1.10 kg) was dissolved in dichloromethane (5.5 L) in a suitable vessel equipped with mechanical stirring, ice bath for cooling and maintained under a blanket of nitrogen. Stirring was started and the reaction mixture was cooled to 0 to −5° C. Concentrated sulfuric acid (1.75 L) was added dropwise over a period of 1 hour into the above mixture, maintaining the temperature below 0° C.; a clear solution was obtained after the addition was complete. The temperature of the reaction mixture was raised to 25 to 27° C. and stirred overnight (12-14 h). Completion of the reaction was determined by HPLC. The reaction mixture was poured slowly over crushed ice (~15.0 kg) and was neutralized with aqueous ammonia (~25% by volume). The aqueous layer was separated and extracted with dichloromethane (2×3.0 L). The combined dichloromethane layer was washed with water (1×12.0 L) followed by brine (1×3.0 L). The product rich organic layer was dried over sodium sulfate and concentrated under reduced pressure to yield 0.85 kg (72.0%) of the crude title compound $^1$H NMR (CDCl$_3$) (400 MHz) (Mixture of diasteromers) δ 1.36 (d&m, 4H, CH$_3$ (J=8.0 Hz & 1H of CH$_2$), 1.90 (m, 1H of CH$_2$), 2.15 & 2.35 (two m, 1H each of CH$_2$—CF$_3$), 2.80-2.90 (m, 1H, CH-Ph), 3.60-3.70 (m, 1H, —(CONH$_2$)CH(NH), 5.90 & 6.45 (1H each of CONH$_2$ with minor peaks for other diasteromer), 7.20-7.40 (m, 6H, Ar+NH).

Step D. (R)-5,5,5-Trifluoro-2-((R)-1-phenylethylamino)pentanamide hydrochloride

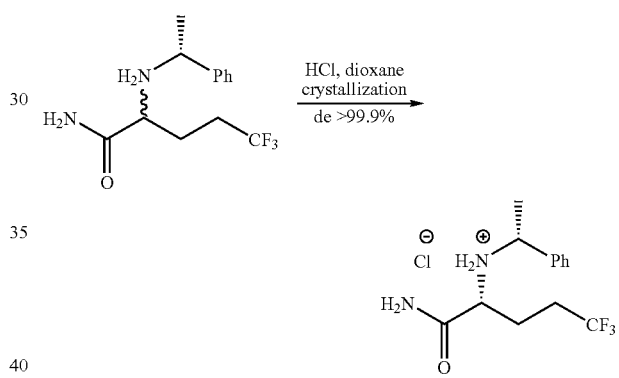

5,5,5-Trifluoro-2-(1-phenylethylamino)pentanamide (mixture of diastereomers) (850 g) was charged into a suitable vessel equipped with mechanical stirring and cooling bath. Methanol (2.55 L), ethyl acetate (1.7 L) and water (1.06 L) were charged and the reaction mixture was cooled to 0 to 5° C. A solution of HCl in dioxane (4.5 M, 1.72 L) was added dropwise over a period of 30 to 45 minutes. Similarly, mixtures of isopropanol and methyl tert-butyl ether could be used as solvent, and aqueous or concentrated HCl could be used as the HCl source. The temperature of the reaction mixture was then raised to 25 to 27° C. and stirred for 2 hours. Completion of the reaction was determined by TLC. The solid that precipitated was filtered and the cake was washed with a suitable solvent, such as ethyl acetate (1.8 L) followed by petroleum ether (2.5 L), or a mixture of isopropanol and methyl tert-butyl ether. The solid was allowed to dry at ambient temperature in an open tray, giving the title R-amino amide (480 g, 50% yield, diastereomeric excess 99.9%) NMR (CDCl$_3$) (400 MHz) δ 1.73 (d, 3H, CH$_3$, J=8.0 Hz), 2.08-2.09 (m, 2H of CH$_2$), 2.20-2.40 (m, 2H, CH$_2$—CF$_3$), 3.50-3.55 (m, 1H, CH-Ph), 4.40-4.41 (m, 1H, —(CONH$_2$)CH(NH), 7.48-7.53 (br s, 5H, Ar).

Step E. (R)-2-Amino-5,5,5-trifluoropentanamide hydrochloride

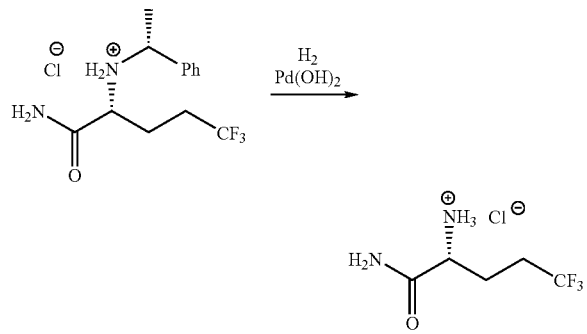

To a suitable pressure vessel, (R)-5,5,5-trifluoro-2-((R)-1-phenylethylamino)-pentanamide hydrochloride (1.50 kg) was charged along with methanol (15.0 L). This was followed by the addition of water (701.0 mL) followed by 20% palladium hydroxide on carbon (225 g). Similarly, palladium on carbon (Pd/C) could be used as the hydrogenation catalyst. The vessel was flushed with nitrogen three times, and then hydrogen gas was pressurized into the vessel (3-4 kg/cm2) at 60° C. The reaction was monitored for completion by HPLC. Upon completion, the reaction mixture was allowed to cool to 30-35° C. and filtered through a Celite pad, then washed with methanol. The filtrate was then concentrated under reduced pressure. After complete concentration, the remaining reaction mixture was treated with dichloromethane (2.5 L per wash), filtered and dried at 45° C. for 12 hours, giving the title compound (915 g, 91.0%; Purity=97%). $^1$H NMR (DMSO-$d_6$) (400 MHz) δ 2.00 (m, 2H, $CH_2$), 2.30-2.40 (m, 2H of $CH_2$—$CF_3$), 3.85-3.88 (m, 1H, —(CONH$_2$)CH(NH), 7.64 & 8.11 (br s, 1H, each of CONH$_2$), 8.44 (br s, 3H, NH$_3^+$). $^{13}$C NMR (DMSO-$d_6$) (100.0 MHz) δ 169.57, 131.20, 128.45, 125.71, 122.97, 50.91, 29.46, 29.18, 28.89, 28.61, 23.56, 23.53.

Preparation B

(R)-5,5,5-Trifluoronorvaline

Method A. R-Transaminase (Biocatalytics and BMS Transaminases)

A solution containing 5,5,5-trifluoro-2-oxopentanoic acid (100 mg, 0.588 mmoles), R,S-alanine (200 mg, 2.244 mmoles), and 0.02 mM pyridoxal phosphate, in 0.1 M potassium phosphate buffer, pH 7.5, was incubated with R-transaminase AT-103 from Biocatalytics (5 mg, 44 units) or cloned R-transaminase from *Bacillus thuringiensis* SC16569 (0.5 mL, 10 units, BMS transaminase) at 30° C. in a total volume of 5 mL in 15 mL tubes for 44 h. Reaction yields of (R)-5,5,5-trifluoro-2-aminopentanoic acid of 49% and 48% were obtained with AT-103 and BMS transaminases, respectively. Ee was 100% in both cases.

The yields were increased by adding auxiliary enzymes to reduce pyruvate to lactate. Lactate dehydrogenase requires NADH as a cofactor. The NADH was regenerated using formate dehydrogenase. A solution containing 5,5,5-trifluoro-2-oxopentanoic acid (100 mg, 0.588 mmoles), D,L-alanine (200 mg, 2.244 mmoles), 0.02 mM pyridoxal phosphate, sodium formate (68 mg, 1 mmole), NAD (331 mg, 5 µmoles) L-lactate dehydrogenase cloned from rabbit muscle (Biocatalytics LDH-103, 0.107 mg, 15 units), and formate dehydrogenase (0.5 mL, 15 units cloned from *Pichia pastoris* and expressed in *Escherichia coli*) in 0.1 M potassium phosphate buffer, pH 7.5, was incubated with R-transaminase AT-103 from Biocatalytics (5 mg, 44 units) or cloned R-transaminase from *Bacillus thuringiensis* SC 16569 (0.5 mL, 10 units) at 30° C. in a total volume of 5 mL in 15 mL tubes. Reaction yields of (R)-5,5,5-trifluoro-2-aminopentanoic acid of 94% and 91% were obtained with AT-103 and BMS transaminases, respectively. Ee was 100% in both cases.

Method B. (R)-Amino Acid Dehydrogenase (Biocatalytics and BMS)

Procedure 1: 5,5,5-trifluoro-2-oxopentanoic acid (60.00 g, 0.353 moles), NH$_4$Cl (64.19 g, 1.2 moles), glucose (86.4 g, 0.479 moles) and water (975 mL) were charged to a 2-L jacketed reactor. NaOH (36 mL of 10 N) was added and the mixture was stirred with a magnet at 30° C. to dissolve the solids. The pH was about 7. Na$_2$CO$_3$ (12.72 g, 0.12 moles) was added which brought the pH to about 8.5. NADP (458 mg, 0.60 mmoles), glucose dehydrogenase (33.7 mg, 5277 units from Amano Enzyme Company), and R-amino acid dehydrogenase (600 mg D-AADH-102, from Biocatalytics) were then added in that order. The reaction mixture was brought to pH 9 by dropwise addition of 10 N NaOH. The reaction mixture was stirred at 30° C. and maintained at pH 9.00 by addition of 5 N NaOH from a pH stat. After 21 h the solution yield of (R)-5,5,5-trifluoro-2-aminopentanoic acid was 51.1 g, 84.7% yield, 100% ee.

Procedure 2: 5,5,5-trifluoro-2-oxopentanoic acid (60.00 g, 0.353 moles), NH$_4$Cl (64.19 g, 1.2 moles), glucose (86.4 g, 0.479 moles) and water (975 mL) were charged to a 2-L jacketed reactor. NaOH (36 mL of 10 N) was added and the mixture was stirred with a magnet at 30° C. to dissolve the solids. The pH was about 7. Na$_2$CO$_3$ (12.72 g, 0.12 moles) was added which brought the pH to about 8.5. NADP (458 mg, 0.60 mmoles), glucose dehydrogenase (33.7 mg, 5277 units from Amano Enzyme Company), and D-amino acid dehydrogenase (50 mL extract containing 1500 units, BMS enzyme) were then added in that order. The reaction mixture was brought to pH 9 by dropwise addition of 10 N NaOH. The reaction mixture was stirred at 30° C. and maintained at pH 9.00 by addition of 5 N NaOH from a pH stat. After 15 h the solution yield of (R)-5,5,5-trifluoro-2-aminopentanoic acid was 51.04 g, 84.6% yield, 99.1% ee.

Preparation C

4-(Bromomethyl)-3-fluorobenzonitrile

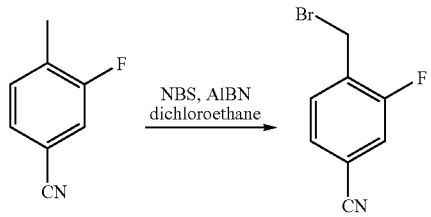

Method A. NBS/AIBN Bromination 1,2-Dichloroethane (151 kg) was charged to a suitable vessel along with 4-cyano-2-fluorotoluene (24 kg) and AIBN (2 kg). The mixture was heated to 70~74° C. Once the batch temperature reached 70° C., N-bromosuccinimide (47.4 kg) was added in portions at the rate of 12 kg/h, maintaining the temperature at 70~74° C. (it is important to control addition rate to avoid exothermic reaction). The mixture was sampled via GC detection after 24 kg of N-bromosuccinimide was added, and the reaction was heated at 70-74° C. until complete reaction was observed. The mixture was cooled to 0-5° C. and allowed to stand for 2 additional hours. The mixture was filtered, and the cake was washed with MTBE (24 kg). The filtrate was washed with water (3×65 kg). The organic layer was dried with sodium sulfate (10.3 kg) for 6 hours, filtered and the cake was washed with MTBE (24 kg). The solution was evaporated under reduced pressure, ethanol (12 kg) was added and the mixture was heated to 40-45° C., then cooled slowly to 0-5° C. while stirring to crystallize. The mixture was filtered and the cake was washed with cold ethanol (5 kg). The crude solid was recrystallized from petroleum ether, filtered and washed with petroleum ether (10 kg), giving the title compound 4-(bromomethyl)-3-fluorobenzonitrile as an off white solid (21 kg, 55% yield). $^1$H NMR (300 MHz, CDCl$_3$) δ ppm 4.46-4.50 (m, 2H) 7.36 (dd, J=8.85, 1.32 Hz, 1H) 7.44 (dd, J=7.91, 1.32 Hz, 1H) 7.52 (dd, J=7.91, 7.16 Hz, 1H). $^{13}$C NMR (75 MHz, CDCl$_3$) δ ppm 23.65 (d, J=4.60 Hz, 1C) 113.76 (d, J=9.77 Hz, 1C) 117.09 (d, J=2.87 Hz, 1C) 119.44 (d, J=24.71 Hz, 1C) 128.44 (d, J=4.02 Hz, 1C) 130.66-130.81 (s, 1C) 130.81-131.06 (s, 1C) 132.18 (d, J=3.45 Hz, 1C) 159.86 (d, J=254.03 Hz, 1C). IR: (KBr) 3088, 3077, 3040, 2982, 2250, 1571, 1508, 1439, 1248 cm$^{-1}$.

Anal. Calcd for C$_8$H$_5$BrFN: Calc. C, 44.89; H, 2.35; N, 6.54; F, 8.88. Found: C, 44.94; H, 2.73; N, 6.56; F, 8.73.

Method B. Sodium Bromate Bromination

To a suitable reactor was added dichloromethane (40 L) and 3-fluoro-4-methylbenzonitrile (4 kg, 18.7 mol) followed by a solution of sodium bromate in water (13.45 kg, 89.1 mol dissolved in 53.6 L water). The reaction mixture was cooled to 0-5° C. A solution of sodium bisulfite (9.25 kg dissolved in 42 L water) was added over a period of 2-3 hours while maintaining a batch temperature of 10-20° C. (the reaction is exothermic). After the addition was complete, a 200 W lamp was shined on the reactor and the batch temperature was increased to 25-30° C. The light and temperature were continued until product was 70-75% by HPLC. The light was removed, stirring was stopped and the reaction was permitted to settle for 15 minutes. The organic layer was removed and the remaining aqueous layer was extracted with dichloromethane twice. The organic layers were combined and washed four times with 10% sodium thiosulfate solution. The organic layer was then washed with brine (10 L) and dried with sodium sulfate. The organic layer was concentrated and then petroleum ether was added and distilled to dryness twice to remove all dichloromethane. Petroleum ether (3 L) was added and the slurry was cooled to 5-10° C. for 1 hour. The slurry was filtered and washed with cold petroleum ether. The product was dried in a vacuum oven at 40-45° C. to give the title compound (3.2 kg, 50.4% yield) as an off-white solid.

Representative procedure for recovery of the title compound from mother liquor: The crude mass (~36% 4-(bromomethyl)-3-fluorobenzonitrile and ~59% gem-dibromide) obtained from concentration of mother liquor (300 g) and 2 equivalents of diisopropyl ethyl amine (based on gem-dibromide) was dissolved in acetonitrile (3 L) and water (50 mL). The reaction was cooled to 0-5° C. and diethyl phosphite (169 g, 1.22 mol) was added over 30 minutes (addition was exothermic). The reaction was stirred for 60-90 min at 0-5° C. and was monitored by TLC. When dibromide was no longer present by TLC, water (3.3 L) was added and the resulting slurry was filtered. The filter cake was washed with water and dried in a vacuum oven (until the moisture content was <1%) to give 202 g (98 AB by HPLC) of additional title compound.

Preparation D (R)-2-(4-Chlorophenylsulfonamido)-5,5,5-trifluoropentanamide

Step A. 5,5,5-Trifluoro-2-(1-phenylethylamino)pentanenitrile

To a solution of (R)-phenethylamine (9.60 g, 79.4 mmol) and acetic acid (5.08 g, 79.6 mmol) in MeOH (150 mL) was added NaCN (3.88 g, 79.6 mmol). The reaction was cooled to 0° C. and a solution of 4,4,4-trifluorobutyraldehyde (10.0 g, 79.6 mmol) in MeOH (50 mL) was added. The reaction was warmed to room temperature and stirred for 20 h. The reaction was diluted with water (400 mL) and extracted with CH$_2$Cl$_2$ (3×300 mL). The combined organic layer was dried over Na$_2$SO$_4$ and concentrated under vacuum to provide the aminonitrile title compound (18.1 g, 89%, as a 4:1 mixture of diastereomers) as a pale yellow oil: $^1$H NMR (300 MHz, CD$_3$OD) δ 7.38-7.27 (m, 5H), 4.15-4.02 (m, 1H), 3.69 (t, J=7.5 Hz, 0.22H), 3.18 (t, J=7.5 Hz, 0.78H), 2.48-2.26 (m, 1H), 2.25-2.03 (m, 1H), 2.01-1.86 (m, 2H), 139 (d, J=6.5 Hz, 2.34H), 1.36 (d, J=6.5 Hz, 0.66H); ESI MS m/z 257 [C$_{13}$H$_{15}$F$_3$N$_2$+H].

Step B. (R)-5,5,5-Trifluoro-2-((R)-1-phenylethylamino)pentanamide hydrochloride

To a solution of 5,5,5-trifluoro-2-(1-phenylethylamino) pentanenitrile (18.0 g, 70.31 mmol, 4:1 mixture of diastereomers) in CH$_2$Cl$_2$ (100 mL) was added H$_2$SO$_4$ (100 mL). The reaction was stirred at room temperature for 22 h, poured onto crushed ice and neutralized with NH$_4$OH. The mixture was extracted with EtOAc (3×500 mL). The combined organic layer was dried over Na$_2$SO$_4$ and concentrated under vacuum to provide the free base of the title compound as a mixture of diastereomers (18.94 g, 98%) as an orange oil: $^1$H NMR (300 MHz, CDCl$_3$) δ 7.40-7.18 (m, 5H), 6.78 (br s, 0.23H), 6.50 (br s, 0.77H), 6.00 (br s, 0.77H), 5.81 (br s, 0.23H), 3.82 (q, J=6.5 Hz, 0.23H), 3.70 (q, J=6.5 Hz, 0.77H), 3.14 (t, J=6.0 Hz, 0.23H), 2.86 (t, J=7.0 Hz, 0.77H), 2.35-1.86 (m, 2H), 1.84-1.64 (m, 2H), 1.39 (d, J=6.5 Hz, 0.69H), 1.35 (d, J=6.5 Hz, 2.31H); ESI MS ink 275 [C$_{13}$H$_{17}$F$_3$N$_2$O+H].

Hydrochloride Salt

To a solution of the free base of the title compound as a mixture of diastereomers (11.9 g, 43.4 mmol) in Et$_2$O/MeOH (7:1, 40 mL) was added a solution of 1 N HCl in Et$_2$O (70 mL). The white precipitate fowled was re-dissolved by heating the mixture and adding MeOH (to a final ratio of 4:1 Et$_2$O/MeOH). The solution was allowed to cool to room temperature and left to stand overnight. The aminoamide hydrochloride salt of the title compound was isolated as a single diastereomer (3.11 g, 23%) as a white solid: $^1$H NMR (300 MHz, CD$_3$OD) δ 7.93 (br s, 1H), 7.69 (br s, 1H), 7.54-7.44 (m, 5H), 4.39 (q, J=7.0 Hz, 1H), 3.50 (t, J=6.5 Hz, 1H), 2.29-2.20 (m, 2H), 2.10-2.01 (m, 2H), 2.07 (d, J=7.0 Hz, 3H); ESI MS m/z 275 [C$_{33}$H$_{17}$F$_3$N$_2$O+H].

Step C. (R)-2-(4-Chlorophenylsulfonamido)-5,5,5-trifluoropentanamide

To a solution of (R)-5,5,5-trifluoro-2-(R)-1-phenylethylamino)pentanamide hydrochloride (3.10 g, 10.0 mmol) in EtOH (100 mL) was added Pd(OH)$_2$ (350 mg) and water (10 mL). The reaction mixture was hydrogenated (40 psi) for 4 h at 50° C. The reaction was filtered through celite and the filtrate was concentrated under vacuum to afford the intermediate amine hydrochloride as a white solid. To a suspension of the amine in CH₂Cl₂ (100 mL) was added N,N-diisopropylethylamine (5.25 mL, 30.0 mmol) and 4-chlorobenzenesulfonyl chloride (2.53 g, 12.0 mmol). The reaction was stirred at room temperature for 18 h. and diluted with EtOAc (200 mL), washed with NaHCO₃ (250 mL) and brine (250 mL), dried over Na₂SO₄, and concentrated under vacuum. The title compound (2.91 g, 84%) was obtained as a white solid by trituration of the residue with CH₂Cl₂/hexanes (2:1): $^1$H NMR (300 MHz, CD₃OD) δ 7.84 (dt, J=8.5, 2.0 Hz, 2H), 7.55 (dt, J=8.5, 2.0 Hz, 2H), 3.85 (dd, J=8.5, 5.0 Hz, 1H), 2.34-2.05 (m, 2H), 1.97-1.68 (m, 2H); ESI MS m/z 345 [C₁₁H₁₂ClF₃N₂O₃S+H].

Preparation E (R)-2-(4-Chloro-N-(4-cyano-2-fluorobenzyl)phenylsulfonamido)-5,5,5-trifluoropentanamide Step A. 4-(Bromomethyl)-3-fluorobenzonitrile To a solution of 3-fluoro-4-methylbenzonitrile (5.0 g, 0.23 mol) in 100 mL of carbon tetrachloride was added N-bromosuccinimide (4.97 g, 0.28 mol) and AIBN (100 mg, 0.61 mmol) and the mixture was refluxed for six hours. The reaction was cooled and filtered. The filtrate was washed with water, dried over magnesium sulfate, filtered and the solvents were removed under vacuum to afford 5.44 g of the title compound as an off-white solid. $^1$H NMR indicated the presence of 20% starting material. $^1$H NMR (400 MHz, CDCl₃) for the title compound: δ 7.54-7.30 (m, 3H), 4.83 (s, 2H).

Step B. (R)-2-(4-Chloro-N-(4-cyano-2-fluorobenzyl)phenylsulfonamido)-5,5,5-trifluoropentanamide To a solution of (R)-2-(4-chlorophenylsulfonamido)-5,5,5-trifluoropentanamide (6.88 g, 20.0 mmol) and 4-(bromomethyl)-3-fluorobenzonitrile (6.43 g, 30 mmol) in DMF (35 mL) was added anhydrous Cs₂CO₃ (19.56 g, 60 mmol). The resulting mixture was stirred at room temperature for 45 min. and then diluted with EtOAc (200 mL), washed with water (100 mL×4) and dried over Na₂SO₄. The product was purified by Biotage (40+M column, 3% to 80% EtOAc in hexanes, 651 mL). The title compound was obtained as a white solid (6.50 g, 68.1% yield). $^1$H NMR (DMSO-d₆, 400 MHz) δ 7.80-7.88 (m, 3H), 7.70-7.75 (m, 2H), 7.67 (d, 2H, J=8), 7.60 (s, 1H), 7.26 (s, 1H), 4.99 (d, 1H, J=16), 4.68 (d, 1H, J=16), 4.14 (t, 1H, J=8), 1.99-2.17 (m, 2H), 1.80-1.94 (m, 1H), 1.40-1.56 (m, 1H). LC/MS M+H 478.14, 94%.

Preparation F (R)-2-(4-Chlorophenylsulfonamido)-5,5,5-trifluoropentanamide

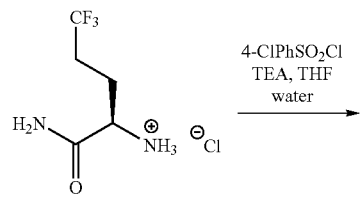

4-ClPhSO₂Cl
TEA, THF
water

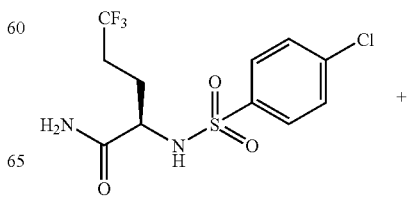

+

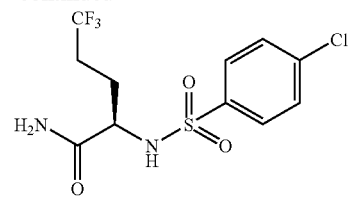

To a suitable dry vessel was added (R)-2-amino-5,5,5-trifluoropentanamide hydrochloride (199.52 g 0.966 mol, 1.0 equiv) followed by 4-chlorobenzenesulfonyl chloride (215.22 g 0.989 mol, 1.02 equiv, 97% w/w %) and 1.6 L of THF at room temperature. Triethylamine (206.5 g, 2.04 mol, 2.1 equiv.) was added over 20 min, maintaining the pot temperature at 15-25° C., and the resulting white slurry was stirred at 15-25° C. for 30 min. Water (1.4 L, 7 vol) of was added to the reaction mixture at 20-25° C. and then THF (1.4 L, 7 vol) was removed by distillation under vacuum (the pot temperature was maintained at 40-60° C. under 250-400 mmHg during distillation process). When the distillation process was complete, 1.4 L (7 vol) of water was added over 30 min while maintaining the pot temperature at 50-60° C., and the resulting slurry was stirred at 50-60° C. for 30 min and then cooled to 10° C. The slurry was agitated for not less than 1 hour, and the product was filtered. The filter cake was washed with water (600 mL each wash) until the pH of the cake wash measured ≧5. The cake was dried under vacuum at not more than 70° C. (jacket temp.) until the loss on drying is <0.5 w/w %, giving the title compound as a white solid (300 g, 91% yield.) $^1$H NMR (DMSO-d₆) (400 MHz) δ 160-1.90 (two in, 1H each of CH₂), 2.10-2.35 (m, 2H of CH₂—CF₃), 3.85-3.88 (m, 1H, —(CONH₂)CH(NH), 7.13 & 7.37 (br s, 1H, each of CONH₂), 7.61 (m, 2H, Ar—H$_a$), 7.64 (m, 2H, Ar—H$_b$), 8.18 (d, 1H, J=8.0 Hz, NH—SO₂). $^{13}$C NMR (DMSO-d₆) (100.0 MHz) δ 171.75, 140.27, 137.77, 131.71, 129.56, 128.95, 126.22, 55.12, 30.1, 29.82, 29.53, 29.25, 25.82, 25.79.

Example 1

(2R)-2-[[(4-Chlorophenyl)sulfonyl][[2-fluoro-4-(1,2,4-oxadiazol-5-deutero-3-yl)phenyl]methyl]amino]-5,5,5-trifluoropentanamide Step A. (2R)-2-[[(4-Chlorophenyl)sulfonyl][(4-cyano-2-fluorophenyl)methyl]amino]-5,5,5-trifluoropentanamide -continued

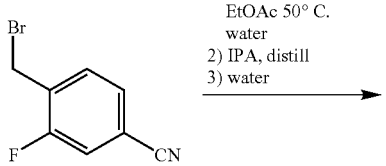

1) K₂CO₃ (2 eq)
Bu₄NBr (0.15 eq)
EtOAc 50° C.
water
2) IPA, distill
3) water

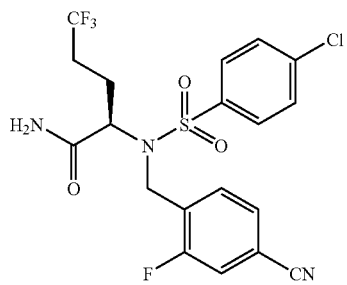

(R)-2-(4-Chlorophenylsulfonamido)-5,5,5-trifluoropentanamide (3.444 kg), potassium carbonate (2.774 kg), tetrabutylammonium bromide (0.484 kg), and 4-(bromomethyl)-3-fluorobenzonitrile (2.092 kg) were charged to a reactor. Ethyl acetate (17.2 L) and water (3.44 L) were then charged and the batch was heated to 50° C. until complete by HPLC (<1 relative Aβ starting material). The reaction is usually complete in about 15 hours. The batch was cooled to 15-20° C. and water (6.88 L) was charged and the bottom aqueous phase was separated. A solution of sodium phosphate monobasic (0.2 M in water, 20.66 L) was charged and the bottom aqueous phase was separated and the pH was tested to ensure that it was <6.5. (Note: If the pH is >6.5, an additional 20.66 L of 0.2 M sodium phosphate monobasic solution may be charged and the extraction and pH measurement repeated.) The solvent was then exchanged by a constant volume vacuum distillation. The reactor was placed under vacuum (270 mmHg) and the jacket was heated to 75-80° C. Once distillation of ethyl acetate started, isopropanol (41.34 L) was added at the same rate of distillate collection, and the overall batch volume was maintained at a constant level. Once all of the isopropanol was added, the vacuum was released and water (13.76 L) was charged. The batch temperature was maintained at approximately 50° C. during the water addition. The batch was then cooled to 15-20° C. and filtered. The wet cake was washed with 50% (v/v) aqueous isopropanol (4×21.6 kg) and then dried under vacuum at 50° C. to give the title compound as an off-white solid (3.648 kg, 78% yield.) $^1$H NMR (300 MHz, DMSO-d₆) δ ppm 1.42-1.55 (m, 1H) 1.80-1.93 (m, 1H) 2.00-2.15 (m, 2H) 4.44 (dd, J=7.91, 1.13 Hz, 1H) 4.68 (d, J=17.71 Hz, 1H) 4.99 (d, J=17.71 Hz, 1H) 7.26 (s, 1H) 7.50 (s, 1H) 7.63-7.73 (m, 4H) 7.78-7.87 (m, 3H). $^{13}$C NMR (75 MHz, DMSO-d₆) ppm 22.58-22.97 (m, 1C) 29.96 (d, J=29.09 Hz, 1C) 41.46 (d, J=5.49 Hz, 1C), 57.86, 110.97, 111.45 (d, J=10.43 Hz, 1C), 117.58, 119.11 (d, J=25.80 Hz, 1C), 124.89, 128.53, 128.56, 129.21, 131.17, 131.98, 137.44, 138.32, 158.99 (d, J=247.54 Hz, 2C), 170.25. $^{19}$F NMR, (CDCl₃, 282 MHz) δ: −116.5, −65.9. IR (KBr): 3443, 3342, 3210, 2955, 2245, 1699, 1577, 1476, 1163 cm$^{-1}$.

Anal. Calcd. for C₁₉H₁₆ClF₄N₃O₃S Calc. C, 47.75; H, 3.37; N, 8.79; S, 6.71; F, 15.90; Cl, 7.41. Found: C, 47.95; H, 3.31; N, 8.67; S, 6.72; F, 15.59; Cl, 7.49.

Step B. (R)-2-(4-Chloro-N-(2-fluoro-4-(N'-hydroxy-carbamimidoyl)benzyl)phenylsulfonamido)-5,5,5-trifluoropentanamide

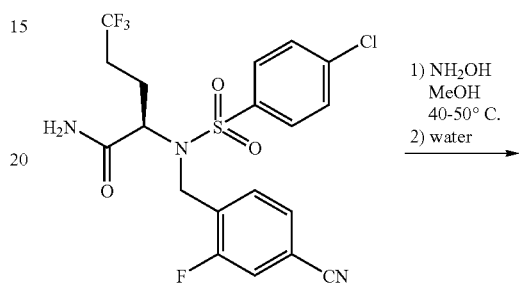

1) NH₂OH
MeOH
40-50° C.
2) water

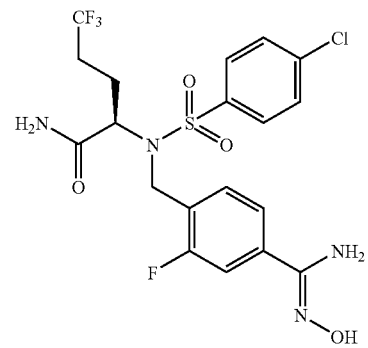

(2R)-2-[[(4-Chlorophenyl)sulfonyl][(4-cyano-2-fluorophenyl)methyl]amino]-5,5,5-trifluoropentanamide (399 g) and methanol (1.6 L) were charged to a reactor followed by hydroxylamine (50% solution in water, 93 mL, 1.8 eq). The mixture was heated to 45-50° C. until complete reaction by HPLC (<0.15 relative Aβ starting material). Water (0.5 L) was charged slowly, keeping the batch temperature between 30-50° C. The batch was allowed to stand until crystallization started and then water (2.7 L) was charged. The batch was cooled to 15-20° C. and filtered. The cake was washed with 2:1 MeOH:water (2 L) and then dried under vacuum at 50° C. to give the title compound as white solid (415 g, 96% yield). $^1$H NMR (300 MHz, DMSO-d₆) δ ppm 1.43-1.64 (m, 1H) 1.77-1.93 (m, 1H) 1.93-2.17 (m, 2H) 4.41 (dd, J=8.48, 6.03 Hz, 1H) 4.60 (d, J=17.14 Hz, 1H) 4.94 (d, J=16.77 Hz, 1H) 5.81-5.98 (m, 2H) 7.19-7.27 (m, 1H) 7.37-7.47 (m, 2H) 7.52 (d, J=4.14 Hz, 2H) 7.64 (d, J=8.67, Hz, 2H) 7.85 (d, J=8.85 Hz, 2H) 9.71-9.83 (m, 1H). IR (KBr): 3491, 3379, 1680, 1651, 1592, 1433, 1343.

Anal. Calcd. for C₁₉H₁₉ClF₄N₄O₄S Calc. C, 44.66; H, 3.74; N, 10.96; S, 6.27; F, 14.87; Cl, 6.94. Found: C, 44.90; H, 3.91; N, 10.91; S, 6.41; F, 15.21; Cl, 6.95.

Step C. (2R)-2-[[(4-Chlorophenyl)sulfonyl][[2-fluoro-4-(1,2,4-oxadiazol-5-deutero-3-yl)phenyl]methyl]amino]-5,5,5-trifluoropentanamide

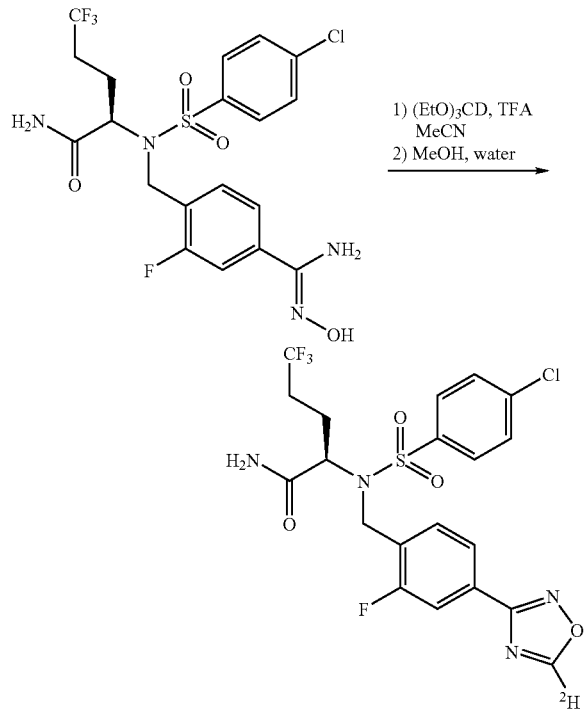

To a solution of (R)-2-(4-Chloro-N-(2-fluoro-4-(1V-hydroxy-carbamimidoyl)benzyl)-phenylsulfonamido)-5,5,5-trifluoropentanamide (500 mg, 0.98 mmol), triethyl orthoformate-D (175 mg, 1.2 mmol) in acetonitrile (5 ml) at 45 degree was added TFA (3.8 μl, 0.049 mmol). The mixture was heated to 60 degree for 90 minutes, and then cooled to RT. The reaction was repeated using 630 mg (1.23 mmol) of (R)-2-(4-Chloro-N-(2-fluoro-4-(N'-hydroxy-carbamimidoyl)benzyl)-phenylsulfonamido)-5,5,5-trifluoropentanamide, 220 mg (1.5 mmol) of triethyl orthoformate-D and 4.5 μL (0.06 mmol) of TFA in acetonitrile (5 mL) using the same conditions. The reaction mixtures were combined and evaporated, and the resulting solid was purified by HPLC (Phenomenex Luna 100×30 mm, 0% MeOH—H$_2$O 0.1% TFA to 100% MeOH—H$_2$O 0.1% TFA in 15 minutes) to give a white solid (950 mg, 1.82 mmol, 83%). $^1$H NMR (500 MHz, CDCl$_3$) δ ppm 8.0-7.9 (m, 1H), 7.8-7.7 (m, 3H), 7.7-7.6 (m, 1H), 7.6-7.5 (m, 2H), 6.4 (s, 1H), 5.4 (s, 1H), 4.7-4.6 (d, 1H), 4.6-4.5 (d, 1H), 4.5-4.3 (q, 1H), 2.3-2.2 (m, 1H), 2.1-1.9 (m, 1H), 1.9-1.8 (m, 1H), 1.6-1.5 (m, 1H). MS (LCMS) [M+H]= 521.98. Integration of the residual oxadiazole proton signal indicated the presence of ~1% proton isotopic analog.

What is claimed is:

1. The compound which is (2R)-2-[[(4-chlorophenyl)sulfonyl][[2-fluoro-4-(1,2,4-oxadiazol-5-deutero-3-yl)phenyl]methyl]amino]-5,5,5-trifluoropentanamide.

2. A pharmaceutical composition comprising a therapeutically effective amount of (2R)-2-[[(4-chlorophenyl)sulfonyl][[2-fluoro-4-(1,2,4-oxadiazol-5-deutero-3-yl)phenyl]methyl]amino]-5,5,5-trifluoropentanamide in association with a pharmaceutically acceptable adjuvant, carrier or diluent.

3. A method for the treatment or delaying the onset of Alzheimer's disease, cerebral amyloid angiopathy, mild cognitive impairment and/or Down syndrome which comprises administering to a mammal in need thereof a therapeutically effective amount of (2R)-2-[[(4-chlorophenyl)sulfonyl][[2-fluoro-4-(1,2,4-oxadiazol-5-deutero-3-yl)phenyl]methyl]amino]-5,5,5-trifluoropentanamide.

4. The method of claim 3 for the treatment of Alzheimer's disease.

5. A method for the treatment of head trauma, traumatic brain injury, and/or dementia pugilistica, which comprises administering to a mammal in need thereof a therapeutically effective amount of (2R)-2-[[(4-chlorophenyl)sulfonyl][[2-fluoro-4-(1,2,4-oxadiazol-5-deutero-3-yl)phenyl]methyl]amino]-5,5,5-trifluoropentanamide.

6. The method of claim 5 for the treatment of head trauma.

7. The method of claim 5 for the treatment of traumatic brain injury.

8. The method of claim 5 for the treatment of dementia pugilistica.

* * * * *